United States Patent [19]

Green et al.

[11] Patent Number: 4,731,106
[45] Date of Patent: Mar. 15, 1988

[54] FUNGICIDAL AZOLE COMPOUNDS

[75] Inventors: David E. Green, Linton; Albert Percival, Hauxton, both of England

[73] Assignee: Schering Agrochemicals Limited, England

[21] Appl. No.: 28,974

[22] Filed: Mar. 23, 1987

Related U.S. Application Data

[63] Continuation-in-part of Ser. No. 801,480, Nov. 11, 1985, abandoned.

[30] Foreign Application Priority Data

Nov. 24, 1984 [GB] United Kingdom ............... 8429739

[51] Int. Cl.⁴ .................. A01N 43/54; A61K 31/505; C07D 403/04
[52] U.S. Cl. ........................................ 71/92; 514/260; 424/46; 544/285; 544/290
[58] Field of Search ............................. 544/290; 71/92; 514/260

[56] References Cited

U.S. PATENT DOCUMENTS

| | | | |
|---|---|---|---|
| 3,322,756 | 5/1967 | Ruschig et al. | 544/290 |
| 3,525,748 | 8/1970 | Pesson et al. | 544/290 |
| 4,055,642 | 11/1977 | Nesvadba et al. | 544/284 |
| 4,269,834 | 5/1981 | Nauta | 544/284 |
| 4,377,581 | 3/1983 | Hess et al. | 544/284 |
| 4,419,357 | 12/1983 | Peet et al. | 544/284 |
| 4,644,000 | 2/1987 | Gaüss et al. | 544/284 |

OTHER PUBLICATIONS

El-Sherief, et al., "Chemical Abstracts", vol. 99, 1983, col. 99:105201p.
Kottke, et al., "Chemical Abstracts", vol. 99, 1983, col. 99:158451b.
Kottke, et al., "Chemical Abstracts", vol. 103, 1985, col. 103:2254/z.
Kottka et al., "Chemical Abstracts", vol. 104, 1986, col. 104:207299r.
Green, et al., "Chemical Abstracts", vol. 105, 1986, col. 105:97495n.

*Primary Examiner*—Glennon H. Hollrah
*Assistant Examiner*—James H. Turnipseed
*Attorney, Agent, or Firm*—Ostrolenk, Faber, Gerb & Soffen

[57] ABSTRACT

Compounds of the formula:

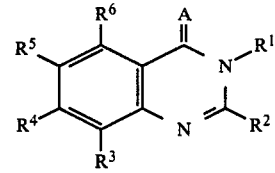

where:
A is oxygen or sulphur;
$R^1$ is phenyl or substituted phenyl in which the substituent is at least one member selected from the group consisting of halogen, $C_{1-6}$-alkyl, $C_{1-6}$-haloalkyl, $C_{1-6}$-alkoxy, $C_{1-6}$-haloalkoxy and nitro;
$R^2$ is 1-imidazoly of 1,2,4-triazol-1-yl; and
$R^3$, $R^4$, $R^5$ and $R^6$, which may be the same or different, are each hydrogen, halo, $C_{1-6}$-alkyl or $C_{1-6}$-alkoxy have valuable fungicidal properties.

10 Claims, No Drawings

FUNGICIDAL AZOLE COMPOUNDS

This application is a continuation-in-part of our application Ser. No. 801,480, filed Nov. 11, 1985 now abandoned.

This invention concerns fungicidal and/or plant growth regulating quinazoline derivatives, processes for their preparation and compositions containing them.

There are numerous examples of imidazole and triazole derivatives having fungicidal activity. Well known products include prochloraz (BP 1469772), triadimefon (BP 1364619) and propiconazole (BP 1522657). We have now found that compounds where an imidazole or triazole group is attached to a quinazoline ring have valuable fungicidal properties. We are not aware of compounds of this type having such activity.

In one aspect, the invention provides a compound of formula I:

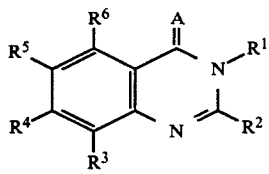

where:
A is oxygen or sulphur;
$R^1$ is phenyl or phenyl substituted in which the substituent is at least one member selected from the group consisting of halogen, $C_{1-6}$-alkyl, $C_{1-6}$-haloalkyl, $C_{1-6}$-alkoxy, $C_{1-6}$-haloalkoxy and nitro;
$R^2$ is 1-imidazolyl or 1,2,4-triazol-1-yl; and
$R^3$, $R^4$, $R^5$ and $R^6$, which may be the same or different, are each hydrogen, halo, $C_{1-6}$-alkyl or $C_{1-6}$-alkoxy.

A is preferably oxygen. Any halogen group is preferably chlorine or fluorine. When $R^1$ is substituted there are preferably one, two, or three substituents. Particularly preferred groups which $R^1$ may represent include phenyl, 4-chlorophenyl and 2,4-dichlorophenyl.

At least two, and preferably three or four, of $R^3$–$R^6$ desirably represent hydrogen. Examples of groups which $R^3$–$R^6$ may represent include fluoro, chloro, bromo, iodo and methyl. Where only one of $R^3$–$R^6$ is other than hydrogen, it is preferably $R^5$. A particularly valuable substituent for $R^5$ is fluorine.

The compounds of formula I may be prepared by reaction of the corresponding compounds of the formula II:

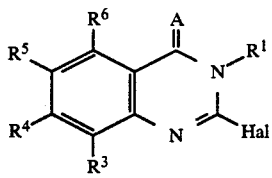

where A, $R^1$, $R^3$, $R^4$, $R^5$ and $R^6$ are as defined hereinbefore and Hal is chlorine or bromine, is reacted with $R^2H$ (i.e. imidazole or 1,2,4-triazole) in the presence of a base to give the desired compound.

The base employed is preferably an alkali-metal hydroxide or carbonate, e.g. potassium carbonate, and the reaction is desirably carried out in a suitable inert solvent medium, e.g. dimethylformamide or acetonitrile.

The compounds of formula II may themselves be prepared by reaction of the corresponding compounds of formula III:

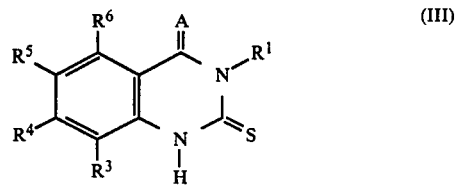

where A, $R^1$, $R^3$, $R^4$, $R^5$ and $R^6$ are as defined hereinbefore, with $SO_2Hal_2$, where Hal is as defined hereinbefore.

The reaction is desirably effected in an inert solvent medium, e.g. chloroform, and with heating, e.g. to reflux.

The compounds of formula III, where A is oxygen, may themselves be prepared by reaction of the corresponding compounds of formula IV:

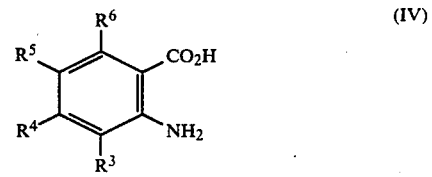

where $R^3$, $R^4$, $R^5$ and $R^6$ are as defined hereinbefore, with an isothiocyanate of the formula $R^1NCS$ where $R^1$ is as defined hereinbefore.

The reaction is desirably effected in an anhydrous aprotic solvent, e.g. ethanol, and with heating, e.g. to reflux.

The compounds of formula III, where A is sulphur, may be prepared from the compounds of formula I, where A is oxygen, by methods known per se, e.g. by reaction with phosphorus pentasulphide or Lawesson's reagent.

The compounds of formula IV are either known or may be prepared from known compounds by methods known per se.

The compounds of formula II may alternatively be prepared by a process in which a compound of formula V:

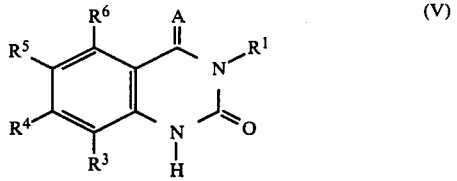

where A, $R^1$, $R^3$, $R^4$, $R^5$ and $R^6$ are as defined hereinbefore, is reacted in the presence of a base with $POHal_3$, where Hal is as defined hereinbefore.

The base employed is preferably an organic base, e.g. pyridine.

The compounds of formula V may themselves be prepared by reaction of the compounds of formula VI:

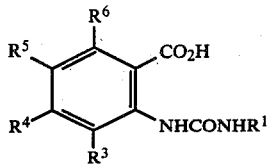

(VI)

where $R^1$, $R^3$, $R^4$, $R^5$ and $R^6$ are as defined hereinbefore, with an acid in a suitable solvent medium.

The acid employed is preferably hydrochloric acid, and the solvent is desirably an alkanol, e.g. ethanol.

In their turn, the compounds of formula VI may be prepared from the compounds of formula IV by reaction thereof with an isocyanate of formula $R^1NCO$ where $R^1$ is as defined hereinbefore.

The quinazoline derivatives of formula I are fungicidal, possessing activity inter alia against a wide range of phytopathogenic fungi, particularly phycomycetes, deuteromycetes, ascomycetes and basidiomycetes orders, and wide range of fungi, e.g. powdery mildew (*Erysiphe graminis*) on cereal crops such as wheat, barley, oats and rye and other cereal diseases such as glume blotch (*Septoria nodorum*), leaf blotch (*Rhynchosporium secalis*), eyespot (*Pseudocercosporella herpotrichoides*), rusts (e.g. *Puccinia graminis*) and take-all (*Gaeumannomyces graminis*). Some compounds of the present invention can be used to control seed borne organisms such as bunt (*Tilletia caries*) on wheat, loose smut (*Ustilago nuda* and *Ustilago hordei*) on barley and oats, leaf spot (*Pyrenophora avenae*) on oats and leaf stripe (*Pyrenophora graminis*) on barley. The compounds can be used against mildews of other crops e.g. vine downy mildew (*Plasmopara viticola*) and powdery mildews, e.g. cucumber powdery mildew (*E. cichoracearum*), apple powdery mildew (*Podosphora leucotricha*) and vine powdery mildew (*Uncinula necator*). They can also be applied to rice for control of rice blast (*Pyricularia oryzae*) and to horticultural crops such as apple trees for the control of apple scab (*Venturia inaequalis*). Other diseases which can be controlled include Botrytis spp., e.g. *Botrytis cinerea* on crops such as vines.

In another aspect, therefore, the invention provides a method of combating fungi at a locus infested or liable to be infested therewith, which comprises applying to the locus an effective amount of one or more compounds of formula I.

The invention also provides a method of regulating the growth of plants which comprises applying to said plants a growth regulating amount of one or more compounds of formula I.

The present compounds are normally employed in the form of compositions containing a surface active agent and/or a carrier.

The compositions will normally be produced initially containing from 0.5 to 99%, preferably from 0.5 to 85%, and more usually from 10 to 50% by weight of the present compounds, which are diluted if necessary before application to the locus to be treated such that the concentration of active ingredient in the formulation applies is from 0.05 to 5% by weight.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, formamide or methylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters; fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise nonionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The compounds of the invention may of course be used in conjunction with one or more further active ingredients, for example compounds known to possess plant-growth regulant, herbicidal, fungicidal, insecticidal or acaricidal properties. Alternatively the compounds of the invention can be used in sequence with the other active ingredient. Fungicides which can be used in conjunction with the compounds of the present invention include maneb, zineb, mancozeb, thiram, ditalimfos, tridemorph, fenpropimorph, fenpropidine, imazalil, propiconazole, triadimefon, triadimenol, diclobutrazol, fluotrimazole, ethirimol, fenarimol, nuarimol, triforine, pyracarbolid, tolclofos-methyl, oxycarboxin, carbendazim, benomyl, thiophanate, thiophanate-methyl, thiabendazole, propineb, metalaxyl, dicloran, dithianon, fuberidazole, dodine, chlorothalonil, cyprofuram, dichlofluanid, sulphur, copper compounds, iprodione, ziram, nabam, prochloraz (and metal complexes of this e.g. the manganese chloride complex), zineb-ethylene thiuram sulphide adduct, captan, captafol, benodanil, mepronil, carboxin, quazatine, validamycin, vinclozolin, tricyclazole, quintozene, pyrazophos, furmecyclox, propamocarb, procymidone, kasugamycin, furalaxyl, folpet, fenfuram, ofurace, etridiazole, fosetyl aluminium, methfuroxam, fentin hydroxide, IBP, cycloheximide, binapacryl, dodemorph, dimethirimol, bupirimate, nitrothal isopropyl, quinomethionate, bitertanol, fluotolanil, etaconazole, fenpropidine, flubenzimine, cymoxanil, flutriafol, fenpentezol, diclopentezol, penconazole, oxadixyl, myclobutanil, flusilazole, hymexazol, anilazine, myclozolin, metomeclan, chlozolinate and benalaxyl.

In the method of the invention, the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable applications rate is within the range of from 0.05 to 20 kg per hectare, more preferably from 0.1 to 10 kg per hectare.

Alternatively the active compound can be applied directly to the plant by, for example, spraying or dusting either at the time when the fungus has begun to appear on the plant or before the appearance of fungus as protective measure. In both such cases, the preferred mode of application is by foliar spraying. It is generally important to obtain good control of fungi in the early stages of plant growth as this is the time when the plant can be most severely damaged. For cereal crops such as wheat, barley and oats, it is often desirable to spray the plant at or before growth stage 5 although additional treatments by spraying when the plant is more mature can augment resistance to the growth or spread of fungi. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.01 to 10 kg. per hectare, preferably from 0.05 to 5 kg per hectare.

The invention is illustrated in the following Examples. Structures of isolated novel compounds were confirmed by elemental and/or other appropriate analyses.

EXAMPLE 1

Phenyl isothiocyanate (28.3 g) was added to anthranilic acid (28.7 g) in absolute alcohol (250 ml) and heated at reflux for 4.5 hours. The mixture was cooled to room temperature and the solid removed by filtration to give 32.5 g of 3-phenyl-2,3-dihydro-2-thioxoquinazolin-4(1H)-one, mp 287°–291° C. Sulphuryl chloride (5.4 ml) was added dropwise at room temperature to a suspension of this product (32.5 g) in chloroform (250 ml). The mixture was heated at reflux for 4 hours. When cool, it was poured into water (400 ml), filtered and the solid washed with dichloromethane. The organic layer was separated from the filtrate, dried and concentrated in vacuo. The residue was extracted with ether, filtered and the filtrate concentrated in vacuo to give an oil which solidified on standing. This was recrystallised from cyclohexane to give crude 2-chloro-3-phenyl-quinazolin-4(3H)-one, mp 102°–5° C. (shown to be 90% pure by high pressure liquid phase chromatography (hplc). A mixture of this product (3.85 g), imidazole (1.02 g) and potassium carbonate (2.07 g) in acetonitrile (60 ml) was heated at reflux for 4 hours. The mixture was cooled to room temperature, and concentrated in vacuo. The residue was chromatographed on silica using light petroleum (bp 60°–80° C.)/ethyl acetate (1:1) as eluant. The resulting solid was recrystallised from cyclohexane to give 0.8 g of 3-phenyl-2-(imidazol-1-yl)-quinazolin-4(3H)-one, mp 163°–5° C. (Compound 1).

EXAMPLE 2

2-(4-Chlorophenylaminocarbonylamino)-5-iodobenzoic acid was prepared by adding a solution of 4-chlorophenyl isocyanate (15.4 g) in ethyl acetate (60 ml) dropwise, at room temperature, to a stirred suspension of 5-iodoanthranilic acid (26.3 g) in ethyl acetate (150 ml). The mixture was heated at reflux for 1 hour, cooled to ambient temperature and the solid removed by filtration, to give 34 g of the substituted benzoic acid. This (34 g) was added to absolute alcohol (250 ml) saturated with hydrogen chloride gas and heated at reflux for 40 minutes. When cool, the solid was filtered and washed with absolute alcohol (50 ml) to give 27.1 g of 3-(4-chlorophenyl)-6-iodoquinazoline-2,4(1H,3H)-dione, mp 324°–6° C. This product (26.9 g) was added slowly to a mixture of pyridine (25 ml) and phosphoryl chloride (250 ml). The mixture was heated at reflux for 6 hours, when a solution developed. When cool, excess phosphoryl chloride and pyridine were removed by distillation in vacuo. The residue was cautiously added to ice water (500 ml) and the solid filtered. This solid was extracted with dichloromethane (100 ml), the extract concentrated in vacuo and chromatographed on silica using dichloromethane to give 9.7 g of 2-chloro-3-(4-chlorophenyl)-6-iodoquinazolin-4(3H)-one, mp 178°–180° C. This was then treated with 1,2,4-triazole and potassium carbonate in a similar manner to Example 1 to give 3-(4-chlorophenyl)-2-(1,2,4-triazol-1-yl)-6-iodoquinazolin-4(3H)-one, mp 206°–208° C. (Compound 2).

EXAMPLE 3

In a similar manner to Example 1 or 2, the following compounds were obtained. In the table, in the column headed $R^2$, Im=imidazolyl and T=1,2,4-triazol-1-yl.

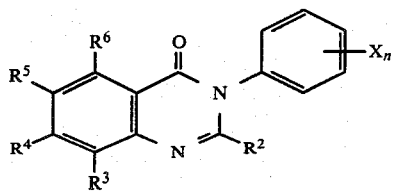

| Cpd | $X_n$ | $R^2$ | $R^3$ | $R^4$ | $R^5$ | $R^6$ | mp (°C.) |
|---|---|---|---|---|---|---|---|
| 3 | 4-Cl | Im | H | H | H | H | 210 |
| 4 | 4-Cl | T | H | H | H | H | 190 |
| 5 | — | T | H | H | H | H | 178–80 |
| 6 | 2,4-Cl$_2$ | T | H | H | H | H | 163–5 |
| 7 | 2,4-Cl$_2$ | Im | H | H | H | H | 135–7 |
| 8 | 4-Cl | T | H | Cl | H | H | 186–8 |
| 9 | 2,4-Cl$_2$ | T | H | H | I | H | 206–8 |
| 10 | 4-Cl | T | H | H | Me | H | 191–4 |
| 11 | 2,4-Cl$_2$ | Im | H | Me | H | Me | 126–30 |
| 12 | 2,4-Cl$_2$ | T | H | H | Cl | H | 192–4 |
| 13 | 2,4-Cl$_2$ | Im | H | H | Cl | H | 212–4 |
| 14 | 2,4-Cl$_2$ | T | H | H | Br | H | 190–4 |
| 15 | 2,4-Cl$_2$ | Im | H | H | Br | H | 229–30 |
| 16 | 4-F | T | H | H | H | H | 170–1 |
| 17 | 4-F | Im | H | H | H | H | 206–8 |
| 18 | 2-Cl | T | H | H | H | H | 159–60 |
| 19 | 2-Cl | Im | H | H | H | H | 173–4 |
| 20 | 4-PhO— | Im | H | H | H | H | 187–8 |
| 21 | 3-CF$_3$ | Im | H | H | H | H | 143–5 |
| 22 | 4-Bu$^t$ | Im | H | H | H | H | 157–9 |
| 23 | 4-PhO— | T | H | H | H | H | 187–9 |
| 24 | 4-Cl—2-Me | Im | H | H | H | H | 153–4 |
| 25 | 2,4-Cl$_2$ | Im | Cl | H | Cl | H | 179–82 |
| 26 | 4-Cl—2-CF$_3$ | T | H | H | H | H | 179–84 |
| 27 | 4-Cl—2-CF$_3$ | Im | H | H | H | H | 159–62 |
| 28 | 2-F | T | H | H | H | H | 100–3 |
| 29 | 2-F | Im | H | H | H | H | 188–9 |
| 30 | 4-Cl—2-Me | T | H | H | H | H | 165–8 |
| 31 | 2,4-Cl$_2$ | Im | H | H | I | H | 234–6 |
| 32 | 2,4,6-Cl$_3$ | T | H | H | H | H | 110–3 |
| 33 | 2,4-Me$_2$ | Im | H | H | H | H | 159–61 |
| 34 | 2,4-Me$_2$ | T | H | H | H | H | 131–3 |
| 35 | 4-CHF$_2$O— | T | H | H | H | H | 177–8 |
| 36 | 2-Me— | T | H | H | H | H | 180–1 |
| 37 | 2-Cl—6-Me | T | H | H | H | H | 174–5 |
| 38 | 2-NO$_2$—4-Cl | T | H | H | H | H | 137–8 |
| 39 | 2,4-F$_2$ | Im | H | H | H | H | 123–5 |
| 40 | 2,4-F$_2$ | T | H | H | H | H | 64–5 |
| 41 | 4-Br | T | H | H | H | H | 209–10 |
| 42 | 4-Br | Im | H | H | H | H | 232–3 |
| 43 | 4-MeO | T | H | H | H | H | 192–4 |
| 44 | 2-Br—4-Cl | T | H | H | H | H | 201–3 |
| 45 | 2-Br—4-Cl | Im | H | H | H | H | 142–4 |
| 46 | 4-NO$_2$ | T | H | H | H | H | 229–31 |
| 47 | 2-Cl—4-Me | T | H | H | H | H | 182–3 |
| 48 | 2-Cl—4-Me | Im | H | H | H | H | 162–4 |
| 49 | 2,6-Cl$_2$ | T | H | H | H | H | 178–9 |
| 50 | 2,6-Cl$_2$ | Im | H | H | H | H | 188–9 |
| 51 | 2,4,6-Me$_3$ | T | H | H | H | H | 123–4 |
| 52 | 2,4,6-Me$_3$ | Im | H | H | H | H | 148–50 |
| 53 | 3-MeO | T | H | H | H | H | 196–8 |
| 54 | 4-Cl | T | H | H | F | H | 181–3 |
| 55 | 2,4-Cl$_2$ | T | H | H | F | H | 191.5–3 |
| 56 | 2,4,6-Cl$_3$ | Im | H | H | H | H | 144–6 |
| 57 | 4-Cl | T | H | Cl | H | Cl | 255–7 |

EXAMPLE 4

A mixture of phosphorus pentasulphide (46.7 g) and 3-(2,4-dichlorophenyl)-2,3-dihydro-2-thioxoquinazolin-4(1H)-one (32.3 g) in xylene (500 ml) was heated at reflux for 4 hours. The hot liquid was then decanted and the residue extracted with boiling xylene (100 ml) and the extract combined with the previously decanted liquid. The extracts were cooled to 5° C. and the orange solid which resulted was removed by filtration. 15 g of this solid was purified on a silica column using petroleum ether (bp 60°–80° C.)/ethyl acetate (1:1) as eluant to give 3-(2,4-dichlorophenyl)-2,3-dihydroquinazoline-2,4(1H,3H)-dithione, mp 218°–20° C. This was then treated with sulphuryl chloride, in a similar manner to Example 1, to give 2-chloro-3-(2,4-dichlorophenyl)-quinazoline-4(3H)-thione which was then treated with 1,2,4-triazole to give 3-(2,4-dichlorophenyl)-2-(1,2,4-triazol-1-yl)-quinazoline-4(3H)-thione, mp 184°–6° C. (Compound 58).

In a similar manner, there was also obtained 3-(2,4-dichlorophenyl)-2-(imidazol-1-yl)-quinazoline-4(3H)-thione, mp 133°–5° C. (Compound 59).

EXAMPLE 5

Compounds of the invention were subjected to various tests (a) Fungicide tests

Compounds are assessed for activity against the following:
  Puccinia recondita: brown leaf rust of wheat (PR)
  Erysiphe graminis: barley powdery mildew (EG)
  Pyricularia oryzae: rice blast (PO)
  Plasmopara viticola: vine downy mildew (PV)

The compounds listed below were formulated in aqueous acetone with Tween 20 wetter to give a concentration of 500 ppm compound/125 ppm wetter/20,000 ppm acetone. For cereals, Pluronic L61 (ethylene oxide/propylene oxide block copolymer) was added (1000 ppm) as an additional wetter. Plants were then treated with the diluted suspensions and then inoculated, 24 hours after treatment with test compound, by spraying with spore suspensions of the fungi and then incubating in a humid atmosphere: >98% RH, as summarised in Table 1.

TABLE 1

| | Environmental conditions during incubation | | | |
|---|---|---|---|---|
| Pathogen | Incubation time (days) | Temperature day / night | Light conditions | Duration of high humidity (days) |
| P. recondita | 12 | 18 / 14 | 1 day dark, 16 hrs light/ 8 hrs dark per day | 1 |
| E. graminis | 9 | 18 / 14 | 16 hrs light/ 8 hrs dark per day | 11 |
| P. oryzae | 7 | 24 / 18 | 3 days dark then 14 hrs light/10 hrs dark per day | 7 |
| P. viticola | 11 | 18 / 14 | As for EG | |

After the appropriate period of incubation, the degree of infection of the leaf surface was visually estimated.

Compounds were considered active if they gave greater then 50% control of the disease at a concentration of 500 ppm (w/v) or less.

(b) Plant growth regulant tests (PGR)

Mung bean (MB) seeds were sown in pots containing coarse grade vermiculite (3–5 seeds per 6 cm pot). Five days later, each pot was placed in approximately 100 ml of an aqueous dispersion of the chemical under test and shoots which had emerged were sprayed to run-off with a portion of test liquid. Eight days later the heights of the seedlings were measured and compared with control plants. Similar tests were also carried out on barley (B) and sunflower (S). Compounds are consided active if they gave a reduction of at least 20% in height compared with controls at rate of 100 mg/L or less.

Activities were demonstrated as follows (+ =active).

| Compound No | FUNGICIDE | | | | PGR | | |
|---|---|---|---|---|---|---|---|
| | EG | PR | PO | PV | MB | B | S |
| 1 | | | + | | | | |
| 2 | + | | | | | | |
| 3 | + | + | | | | | |
| 4 | + | + | | | | | |
| 5 | + | + | | | | | |
| 6 | + | + | | | | | |
| 7 | + | + | | | | | |
| 8 | + | + | | | | | |
| 9 | + | + | | | | | |
| 10 | + | | | | + | + | + |
| 11 | + | + | + | | + | + | |
| 12 | + | + | | | + | + | |
| 13 | + | + | | | + | | |
| 14 | + | + | | | | | |
| 15 | + | + | | | | | |
| 16 | + | | | | | | |
| 17 | + | | | | | | |
| 18 | + | | | | + | + | |
| 19 | + | + | + | | + | + | |
| 20 | + | | | | + | + | |
| 21 | + | | | | | + | |
| 22 | | + | | | + | | |
| 23 | + | | | | + | | |
| 24 | + | + | | | + | + | + |
| 25 | + | | | | | | |
| 26 | + | | | | + | | |
| 27 | + | + | | | + | + | + |
| 28 | + | | | | | | |
| 29 | | | | | + | + | |
| 30 | + | | | | | + | |
| 31 | | + | | | | | |
| 32 | + | | | | | | |
| 33 | + | | | | | | |
| 34 | + | | | | | | |
| 35 | + | | | | | | |
| 36 | + | | | | | | |
| 37 | + | | | | | | |
| 38 | + | | + | | | | |
| 39 | + | + | | | | | |
| 40 | + | | | | | | |
| 41 | + | | | | | | |
| 42 | + | | | | | | |
| 43 | | | | + | | | |
| 44 | + | | | + | | | |
| 45 | + | | + | + | | | |
| 46 | + | | | + | | | |
| 47 | + | | | + | | | |
| 48 | | + | | + | | | |
| 49 | + | | | + | | | |
| 50 | | | | + | | | |
| 51 | | | | + | | | |
| 52 | | | | + | | | |
| 53 | | | | + | | | |
| 54 | + | | | | | | |
| 55 | + | | + | | | | |
| 56 | + | + | + | | | | |
| 57 | + | | | | | | |
| 58 | + | + | | | | | |
| 59 | + | + | | | | | |

EXAMPLE 6

This example illustrates typical concentrates that can be formulated from compounds of the invention.

| (a) Wettable powder | |
|---|---|
| Compound of the invention | 25% w/w |
| Sodium lignosulphonate | 5% w/w |
| China clay | 70% w/w |
| (b) Suspension concentrate | |
| Compound of the invention | 500.0 g/l |
| Synperonic P103[1] | 43.0 g/l |
| Tamol 731[2] | 10.8 g/l |
| Silicone antifoam | 0.6 g/l |
| Sodium acetate | 10.8 g/l |
| Hydrochloric acid | 10.8 g/l |
| Xanthan gum | 1.5 g/l |
| Formaldehyde | 5.4 g/l |
| Water | 598.0 g/l |
| (c) Seed treatment | |
| Compound of the invention | 25% w/w |
| Lake red toner | 1% w/w |
| Liquid paraffin | 2% w/w |
| Talc | 72% w/w |

[1]Polyoxyethylene/oxypropylene block copolymer
[2]Maleic acid/olefine copolymer (25% aq. soln. of sodium salt)

We claim:

1. A compound of formula I:

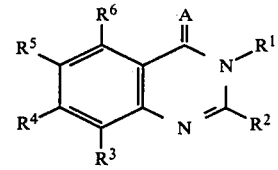

where:

A is oxygen or sulphur;

$R^1$ is phenyl or substituted phenyl in which the substituent is at least one member selected from the group consisting of halogen, $C_{1-6}$-alkyl, $C_{1-6}$-haloalkyl, $C_{1-6}$-alkoxy, $C_{1-6}$-haloalkoxy and nitro;

$R^2$ is 1-imidazolyl or 1,2,4-triazol-1-yl; and $R^3$, $R^4$, $R^5$ and $R^6$, which may be same or different, are each hydrogen, halo, $C_{1-6}$-alkyl or $C_{1-6}$-alkoxy.

2. A compound according to claim 1 in which A is oxygen.

3. A compound according to claim 1 in which $R^1$ is phenyl, 4-chlorophenyl or 2,4-dichlorophenyl.

4. A compound according to claim 1 in which at least three of $R^3$–$R^6$ is hydrogen.

5. A compound according to claim 1 selected from the group consisting of:
3-(4-chlorophenyl)-2-(1,2,4-triazol-1-yl)-quinazolin-4(3H)-one,
3-phenyl-2-(imidazol-1-yl)-quinazolin-4(3H)-one,
3-(2,4-dichlorophenyl)-2-(1,2,4-triazol-1-yl)-quinazolin-4(3H)-one,
3-(2,4-dichlorophenyl)-2-(imidazol-1-yl)-quinazolin-4(3H)-one,
3-(4-chlorophenyl)-6-iodo-2-(1,2,4-triazol-1-yl)-quinazolin-4(3H)-one,
3-(2,4-dichlorophenyl)-6-iodo-2-(1,2,4-triazol-1-yl)-quinazolin-4(3H)-one,
3-(2,4-dichlorophenyl)-6-bromo-2-(1,2,4-triazol-1-yl)-quinazolin-4(3H)-one,
3-(2,4-dichlorophenyl)-6-fluoro-2-(1,2,4-triazol-1-yl)-quinazolin-4(3H)-one,
3-(2,4-dichlorophenyl)-2-(1,2,4-triazol-1-yl)-6-chloroquinazolin-4(3H)-one and
3-(2,4-dichlorophenyl)-2-(imidazol-1-yl)-6-chloroquinazolin-4(3H)-one.

6. A compound according to claim 1 in which A is oxygen; $R_1$ is phenyl, 4-chlorophenyl or 2,4-dichlorophenyl; and in which at least three of $R_3$–$R_6$ are hydrogen and the remaining member of $R_3$–$R_6$ is hydrogen, halogen or methyl.

7. A fungicidal or plant growth regulant composition which comprises a compound claimed in claim 1 in admixture with an agriculturally acceptable diluent or carrier.

8. A composition according to claim 7 in which A is oxygen.

9. A composition according to claim 7 in which $R_1$ is phenyl, 4-chlorophenyl or 2,4-dichlorophenyl.

10. A composition according to claim 7 in which A is oxygen; $R_1$ is phenyl, 4-chlorophenyl or 2,4-dichlorophenyl; and in which at least three of $R_3$–$R_6$ are hydrogen and the remaining member of $R_3$–$R_6$ is hydrogen, halogen or methyl.

* * * * *